United States Patent
Drury

(10) Patent No.: US 10,197,495 B2
(45) Date of Patent: Feb. 5, 2019

(54) URINE ANALYSIS DEVICE, METHOD AND SYSTEM

(71) Applicant: Daniel Gordon Drury, Camp Hill, PA (US)

(72) Inventor: Daniel Gordon Drury, Camp Hill, PA (US)

(*) Notice: Subject to any disclaimer, the term of this patent is extended or adjusted under 35 U.S.C. 154(b) by 0 days.

(21) Appl. No.: 15/637,590

(22) Filed: Jun. 29, 2017

(65) Prior Publication Data
US 2018/0003621 A1    Jan. 4, 2018

Related U.S. Application Data

(60) Provisional application No. 62/356,147, filed on Jun. 29, 2016.

(51) Int. Cl.
| | |
|---|---|
| *G01N 21/29* | (2006.01) |
| *G01N 33/493* | (2006.01) |
| *A47K 13/08* | (2006.01) |
| *E03D 13/00* | (2006.01) |
| *G01J 3/46* | (2006.01) |
| *A61B 5/00* | (2006.01) |
| *A61B 5/103* | (2006.01) |

(52) U.S. Cl.
CPC ........... *G01N 21/293* (2013.01); *A47K 13/08* (2013.01); *E03D 13/005* (2013.01); *G01J 3/46* (2013.01); *G01N 33/493* (2013.01); *A61B 5/1032* (2013.01); *A61B 5/4875* (2013.01)

(58) Field of Classification Search
CPC .... G01N 21/293; G01N 33/493; A47K 13/08; A61B 5/4875; E03D 13/005
See application file for complete search history.

(56) References Cited

U.S. PATENT DOCUMENTS

| 4,103,367 | A |   | 8/1978  | Kaufer |                   |
|-----------|---|---|---------|--------|-------------------|
| 4,976,923 | A | * | 12/1990 | Lipsky | ....... B01L 3/508 |
|           |   |   |         |        | 422/401           |
| 5,365,616 | A | * | 11/1994 | Morad  | ....... E03D 9/032 |
|           |   |   |         |        | 4/222             |

(Continued)

OTHER PUBLICATIONS

Armstrong, Lawrence E., HydrationCheck, 2011 [website], [retrieved on Jul. 1, 2013]. Retrieved from the Internet: <URL: http://www.hydrationcheck.com/products.php>.

(Continued)

*Primary Examiner* — Tri Ton
*Assistant Examiner* — Rufus Phillips
(74) *Attorney, Agent, or Firm* — Buchanan Ingersoll & Rooney PC

(57) ABSTRACT

A urine screen and urine analysis method for analyzing urine color to determine the hydration level of an individual. The urine screen is nonabsorbent. The urine screen includes a base member, a urinal dish, and a color scale. The urinal dish has a side wall that extends from the front side of the base member. The urinal dish is open at the top portion and is able to receive fluid into the urinal dish through the open top portion. The urinal dish includes a small drain hole. The color scale is applied to the front side of the base member and includes at least a plurality of shades of yellow. Each of the shades of yellow corresponds to a hydration level based on urine color.

13 Claims, 10 Drawing Sheets

(56) References Cited

U.S. PATENT DOCUMENTS

| | | | | |
|---|---|---|---|---|
| 6,004,821 A | * | 12/1999 | Levine | B01L 3/5027 |
| | | | | 422/504 |
| 2012/0106811 A1 | * | 5/2012 | Chen | A61B 10/007 |
| | | | | 382/128 |
| 2015/0009502 A1 | * | 1/2015 | Drury | G01N 33/493 |
| | | | | 356/422 |
| 2017/0036204 A1 | * | 2/2017 | Zercher | A61B 10/007 |
| 2017/0055958 A1 | * | 3/2017 | Suarez | A61B 10/007 |

OTHER PUBLICATIONS

Y&R Sao Paulo, Bonafont Water: "STICKER" Promo / PR Ad, released Mar. 2011. Retrieved from Internet on Sep. 19, 2013: <URL: http://www.coloribus.com/adsarchive/promo-casestudy/bonafont-water-sticker-16584055>.

* cited by examiner

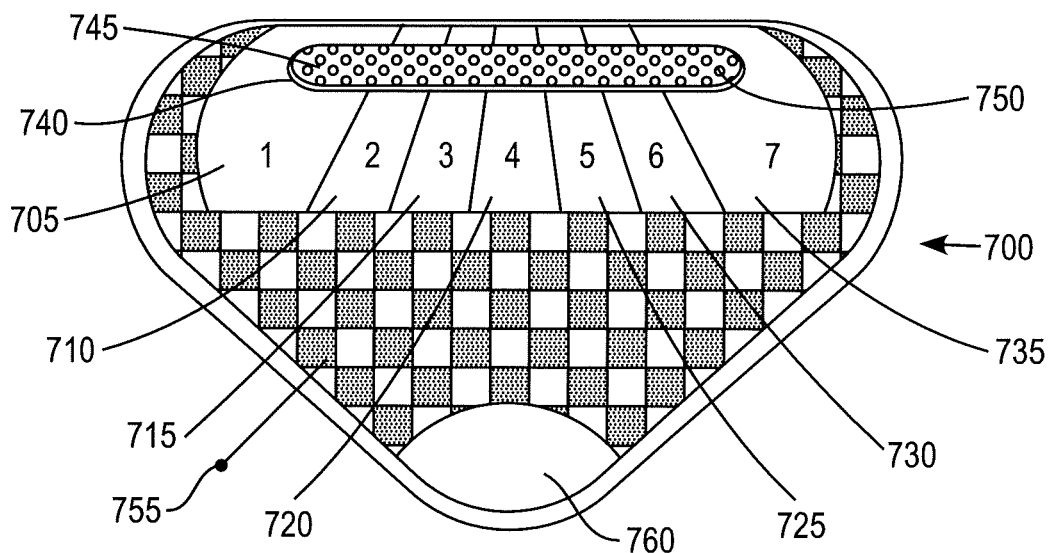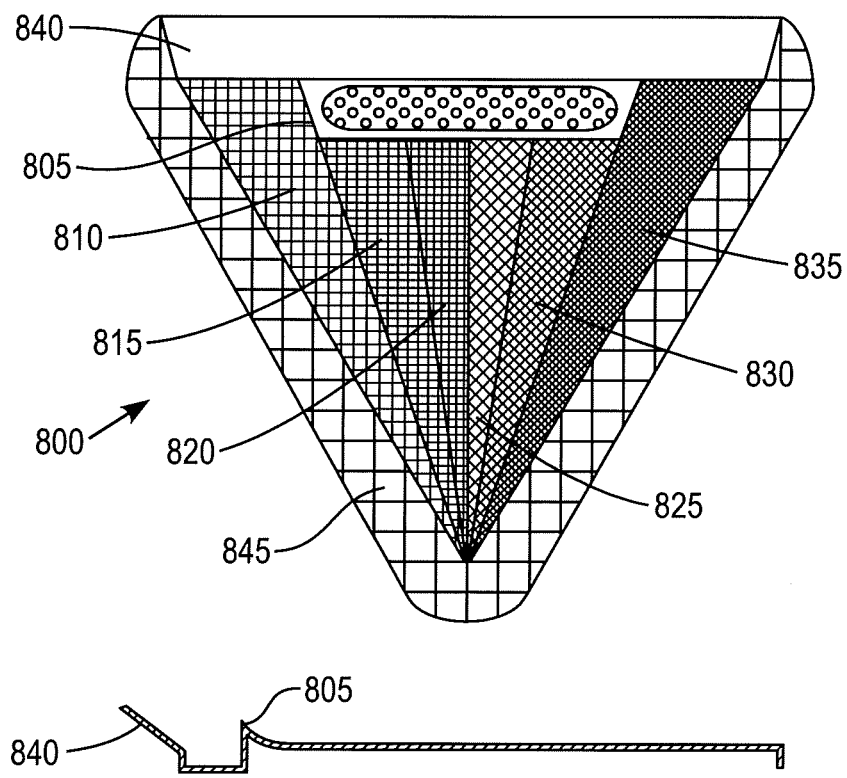

URINE ANALYSIS DEVICE, METHOD AND SYSTEM

CROSS-REFERENCES TO RELATED APPLICATIONS

This application claims priority to U.S. Provisional Application No. 62/356,147 filed on Jun. 29, 2016. The entire contents of this provisional application are incorporated herein by reference.

TECHNICAL FIELD

The present invention relates to a device, method and system for determining the hydration level of an individual based on urine color.

BACKGROUND

Although dehydration is commonly viewed as a condition affecting athletes and manual laborers, dehydration is a health concern for all individuals. Dehydration is especially a concern in places where individuals are susceptible to developing a fluid imbalance and/or thermoregulatory challenge. Examples of locations that may include susceptible individuals are senior centers, public schools, hospitals and national parks.

The hypothalamus inside the brain monitors body temperature. When the hypothalamus detects that heat has begun to accumulate within the body, certain physiological adjustments are made to maintain a healthy body temperature. The dissipation of internal body heat is accomplished in a variety of ways including radiation, convection, conduction and evaporation through sweating. Evaporation is a primary mode of heat transfer during physical exertion and can account for up to 80% of the body's heat loss. In extremely hot conditions, the human body can lose as much as two liters of sweat per hour. If the body's water supply is not replenished continuously, dehydration might occur. In some cases, this can result in dangerous and potentially life-threatening consequences.

A variety of factors affect an individual's sweat rate. These factors include the ambient temperature and humidity, the intensity and duration of the physical exertion, the type of clothing worn by the individual, the individual's fitness level, hereditary factors, and additionally the individual's state of acclimatization and current hydration status. Early warning signs that an individual is entering a state of dehydration include: irritability, vomiting, thirst, headache, dizziness, fatigue, chills and darker than normal urine. If allowed to persist, dehydration can lead to muscle cramps, excessive sweating, heat exhaustion and possibly heat stroke.

An individual's desire to consume fluids (i.e., thirst) is often not an accurate means to gauge the individual's current hydration level. The hypothalamus monitors the body's temperature and controls the physiological response to a thermoregulatory challenge. The hypothalamus is affected by sodium levels, blood osmolality and overall plasma volume. The mechanisms for controlling body temperature are hormonal, physiological, metabolic and behavioral. All of these factors are subject to individual variation. Therefore, it can be difficult to predict the exact amount of fluid an individual should consume to avoid dehydration.

Clinical methods to monitor and diagnose dehydration include tests based on plasma osmolality, urine specific gravity, urine osmolality and various isotope techniques. Field methods for diagnosing dehydration are generally less accurate than clinical methods, but nonetheless provide valuable indicators of dehydration. Field methods include monitoring acute weight loss (e.g., pre-practice vs. post-practice weight), urine color and other typical signs of dehydration (e.g., thirst, dizziness, headache, irritability, etc.).

Urine color can be used to assess an individual's hydration level because urine color may change in response to changes in the individual's overall hydration level. A euhydrated individual (i.e., an individual with normal body water content) typically produces urine which is light yellow or straw color. A dehydrated individual may produce urine that is dark yellow, orange, gold, light brown or brownish-green in color. When the body enters a state of dehydration, there is a deficit between fluid intake and fluid loss. This deficit is reflected by an increased concentration of particulates excreted in the urine. If more water is lost through sweating than is consumed through drinking, less water is available to dilute the particulates in the urine, and so the urine color becomes darker.

Known color scales for analyzing urine color are printed on a paper chart. An individual must collect his or her urine in a clear container and then a medical professional will hold the paper chart next to the urine sample to make the color comparison. Individuals often object to the collection and handling of urine that is required to obtain an accurate measurement. This process is also time consuming in that the urine must first be collected in the clear container and subsequently compared to the paper chart. The process may be difficult for certain individuals (e.g., elderly individuals or younger children). Because known color scales require the collection of urine, these color scales are not helpful to an individual who excretes his or her urine into a urinal or toilet.

Therefore, there is a need for a quicker and less burdensome manner of analyzing urine color. To this end, the present inventor developed a color chart that could be adhered directly to a back surface of a urinal, for instance, which received U.S. Pat. No. 9,068,968. While this color chart is very useful, the present inventor has developed another manner of analyzing urine color that may provide some beneficial improvements, as disclosed herein.

As a final background point, some toilet receptacles may include a smell masking agent. For example, urinals are often provided with urinal screens that hold a urinal deodorizer cake (also known as a urinal deodorizer block, urinal cake, urinal mint, urinal puck, etc.). The urinal screens allows the urinal deodorizer cake to communicate with the environment so that the urinal deodorizer cake may provide a masking odor or reducing odor. The urinal screen with the urinal deodorizer cake is typically placed above the urinal drain. The urinal screen includes openings at the top of the urinal deodorizer cake holding receptacle so that water and/or urine may flow over the urinal deodorizer cake. The urinal deodorizer cake may include a disinfectant so that when the flushing water and/or urine flows over the urinal deodorizer cake, the disinfectant is transferred to the urinal during the flush to disinfect an area of the urinal. For example, U.S. Pat. No. 4,103,367 discloses a urinal screen configured to hold a deodorizing and/or disinfecting chemical block (i.e., a urinal cake). However, conventional urinal screens, such as the screen disclosed in U.S. Pat. No. 4,103,367, do not provide any benefit of enabling a user to readily analyze urine color and hydration level.

SUMMARY

One aspect of the disclosure here involves a urine screen for determining a hydration level of an individual based on urine color. The urine screen is nonabsorbent. The urine screen includes a base member, a urinal dish, and a color scale. The urinal dish has a side wall that extends from the front side of the base member. The urinal dish is open at the top portion and is able to receive fluid into the urinal dish through the open top portion. The urinal dish includes a small drain hole. The color scale is applied to the front side of the base member and includes at least a plurality of shades of yellow. Each of the shades of yellow corresponds to a hydration level based on urine color.

Another aspect of the disclosure here involves a dehydration system for determining a hydration level based on urine color. The dehydration includes a urine collection device and a color scale. The color scale includes a plurality of shades of yellow. Each of the shades of yellow corresponds to a hydration level of a user based on urine color. The urine collection device includes a cylindrical member extending in a vertical direction and a base member attached to the bottom end of the cylindrical member. The top end of the cylindrical member is open. The base member has a small drain hole configured to control outflow of urine such that a user may compare the urine color to the plurality of shades of yellow of the color scale.

Also disclosed is a urine collection dish that is configured to attach to a toilet. The urine collection dish includes an attachment portion to attach the collection dish to the front portion of the toilet. A color scale extends along the upper surface of the attachment portion. The color scale includes a plurality of shades of yellow. Each of the shades of yellow correspond to a hydration level based on urine color. The urine collection dish also includes a dish portion extending from the lower surface of the attachment portion. The dish portion is shaped to collect urine within the toilet bowl of the toilet. The dish portion has a small drain hole to control drainage of urine into the toilet bowl so that a user may compare the urine color in the collection dish to the plurality of shades of yellow of the color scale before the urine drains through the small drain hole.

Also disclosed is a method for determining a hydration level based on urine color. The method includes applying a stream of urine into a urine dish extending from a base member of a urine screen. The urine screen includes a water-resistant color scale applied to or is part of the base member and also includes a drain hole. The method further includes slowly draining the stream of urine through the drain hole of the urine screen so that a portion of the stream of urine is retained in the urine dish, visually comparing the urine color of the portion of the retained urine to a plurality of colors included on the water-resistant color scale, identifying a color included on the water-resistant color scale which most closely matches the urine color of the portion of the retained urine, and determining the hydration level by referencing a hydration level indicator corresponding to the identified color.

BRIEF DESCRIPTION OF THE DRAWINGS

Objects and advantages of the invention will become apparent upon reading the following detailed description of preferred embodiments and upon reference to the drawings, in which:

FIG. 7 is a top view of an embodiment of a urine screen.

FIGS. 8A and 8B are views of an embodiment of a urine screen. FIG. 8A is a top view of the urine screen, and FIG. 8B is a side view of the urine screen of FIG. 8A.

FIG. 10A is a top view of the urine screen, and FIG. 10B is a side view of the urine screen of FIG. 10A.

FIG. 12A is a top view of the urine screen, and FIG. 12B is a perspective view of the urine screen.

DETAILED DESCRIPTION OF PREFERRED EMBODIMENTS

The urinal screen and method disclosed here allow an individual to determine their hydration level while simultaneously urinating into a urine receptacle such as a urinal or toilet. A nonabsorbent urine screen may be placed in a urinal (i.e., within the bowl of the urinal). The device may be nonabsorbent in that it does not absorb or chemically react with urine and/or water. A urinal dish may extend from the center of the base member of the nonabsorbent urine screen to temporarily hold urine. The urinal dish may have one or more drain holes that are sized to drain slowly enough so that the urinal dish retains at least a portion of urine within the urinal dish for a period of time. The nonabsorbent screen further may include a color scale with different colors corresponding to different levels of hydration. After or during urination into the urinal dish of the nonabsorbent urine screen, the individual may be able to visually compare the urine color to the color scale located on the nonabsorbent urine screen. Once the urine color has been matched to the color scale, the individual can refer to a hydration level indicator to determine his or her hydration level. The device may be used by all individuals at any time, including those facing a thermoregulatory challenge due to physical exertion and/or a fluid imbalance or those who may be interested in monitoring their hydration level during activities of daily living.

Figure 1:
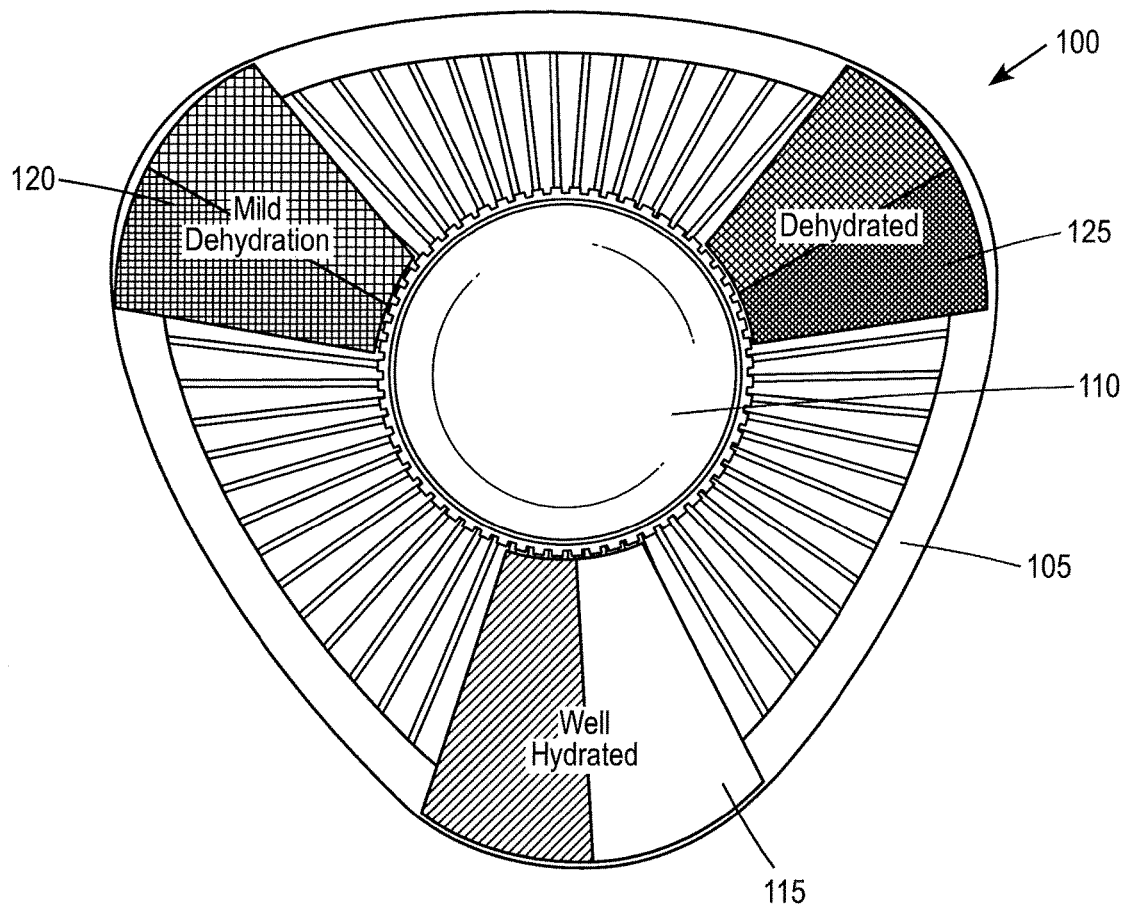
FIG. 1 is a top view of a nonabsorbent urine screen according to an embodiment of the present application.

FIG. 1 illustrates a top view of a nonabsorbent urine screen 100. The urine screen 100 includes a base member 105. The base member 105 may be made out of a flexible material to conform to a deployment location (e.g., to match the contours in the bowl of a urinal) and may be a nonabsorbent material (e.g., the base member 105 will not absorb water or urine). For example, the base member 105 may be formed out of a flexible plastic that does not absorb water. If the base member 105 is made out of an absorbent material such as paper, the exposed surfaces of the base member 105 can be covered with a water-resistant coating or water-resistant layer to prevent absorption of urine and/or water.

The base member 105 may be triangularly shaped with rounded edges as shown in FIG. 1. However, the shape of the base member 105 is not limited to a triangular-shape. For example, the base member could be circular, rectangular, pentagonal, etc. or even an irregular shape. The shapes of the edges of the base member 105 are not limited to rounded edges and can instead be pointed edges, indented edges, etc. The edges of the base member 105 also can be different shapes from one another.

The urine screen 100 may be designed to withstand repeated contact with urine and water. The urine screen 100 may be positioned or disposed within the bowl of a urinal so that urine and water will flush/flow over the urine screen 100 to reach the drain of the urinal.

The urine screen 100 also includes a urinal dish 110. The urinal dish 110 may be disposed at the center of the base member 105, as illustrated in FIG. 1. The urinal dish 110 has a side wall that extends or protrudes from the base member 105. The side wall of the urinal dish 110 may be circular as illustrated in FIG. 1, or the urinal dish may have another wall configuration such as triangular, rectangular, etc. The side wall of the urinal dish 110 in one embodiment may extend 4-5 mm from the base member 105.

The top portion of the urinal dish 110 is able to communicate with the environment so that, for example, a urine stream may enter the urinal dish 110. The top portion of the urinal dish 110 depicted in FIG. 1 is open. In other words, there is no structure above the side walls of the urinal dish 110, so that the urinal dish 110 has an open/uncovered top portion. However, in some embodiments, the top portion of the urinal dish 110 may have a structure that includes holes (i.e., the top portion is porous), slits, or other apertures allowing the urine stream to enter the urinal dish 110. If the top portion of the urinal dish 110 includes any structural features, the top portion may be formed out of a transparent material to allow a user to visually inspect the color of the applied urine.

FIG. 1 also illustrates the color scale, which in the illustrated embodiment consists of the three differently colored regions 115, 120, 125. The well-hydrated region 115 is shaded with the lightest color of the three regions because a urine stream that is lightest in color reflects that the individual is well-hydrated (as described further below). The mild dehydration region 120 is a slightly darker shade of yellow than the well-hydrated region 115. The dehydrated region 125 is the darkest of the three regions 115, 120, 125 to indicate that the individual is dehydrated.

As described above and illustrated in FIG. 1, the color scale may include at least three color regions. However, utilizing a different number of color regions is certainly possible. Each color region 115, 120, 125 may possess a single color (i.e., the region is uniform in color). In one embodiment, the color scale may progressively change from lighter colors to darker colors within each region 115, 120, 125 to reflect a range of shades of yellow that are within that hydration state. For example, the urine color of an individual with mild dehydration is within a range of shades of yellow. The color regions 115, 120, 125 may also be arranged on the base member 105 to be adjacent to one another (e.g., in a row above the urinal dish 110). Each color region 115, 120, 125 in this embodiment may blend into an adjacent color.

The color scale disclosed here includes multiple shades of yellow ranging from light yellow to dark yellow. The darker end of the color scale (e.g., the dehydrated region 125) may include shades of orange, gold, light brown, dark brown, and/or brownish-green. In one embodiment, the color scale includes eight colors having the following color values: (1) 17-B1; (2) 9-H1; (3) 17-J1; (4) 17-L1; (5) 9-IS; (6) 9-L3; (7) 12-K6; and (8) 23-L1. These color values refer to the Classic Compendium of Color discussed in Maerz, A. and Paul, M. R., *Dictionary of Color* (2nd Ed.) New York: McGraw-Hill, 1950 at pages 41-69. The color scale may progressively change between these eight colors, or the color scale may include eight distinct color regions with each region possessing a single one of the eight colors. Other colors can also be can also be used that correspond to various levels of dehydration and these colors can be determined based upon their appearance in the collection dish with a white background. In one embodiment, the well-hydrated region 115 includes color values 17-B1, 9-H1 and 17-J1; the mild dehydration region 120 includes color values 17-L1 and 9-IS; and the dehydrated region 125 includes color values 9-L3, 12-K6 and 23-L1.

Each of the color regions 115, 120, 125 corresponds to a different level of hydration such as euhydration, mild-moderate dehydration and severe dehydration. Each color region 115, 125, 130 may include a hydration level indicator that helps the individual determine their hydration level. The hydration level indicator may be words, numbers and/or a graphic. In FIG. 1, each of the color regions 115, 120, 125 have a word description of the hydration level (e.g., "Well-Hydrated") for that color region 115, 120, 125. The hydration level indicators may be applied or printed directly on the color scale as shown in FIG. 1. The hydration level indicators can also be offset from the color scale. The hydration level indicator could be a reference number that refers to a chart listing reference numbers and descriptions of their corresponding hydration levels (e.g., a placard above the urinal, described below). The hydration level indicators could include a graphic such as an image of a thumbs-up or a thumbs-down. Any combination of these possible indicators or other variants is included. The hydration indicators may be any ink that is water resistant, or the hydration indicators may be covered by a water resistant layer (as described below). The hydration indicators may be applied/fixed by any printing method, such as typographic, flexographic, lithographic, gravure, screen, or non-impact printing.

The bottom of the urinal dish 110 may be a white layer that provides a white background. This bottom surface may either be formed out of a naturally white material (e.g., a white plastic) or the bottom surface may be treated or painted to be a shade of white. The individual can thus view the urine accumulating in the urinal dish 110 over the white background and compare the urine color of the portion in the urinal dish 110 to the color scale provided on the base member 105. Instead of a white background, the bottom surface of the urinal dish 110 could be another light color (e.g., light gray) that allows an individual to visually detect the urine color. The base member 105 itself may be white as well so that the base member 105 color does not create a visual distraction to preclude accurately assessing the color shades of the color regions 115, 120, 125 when making the comparison.

In one embodiment, the bottom of the urinal dish 110 may itself have the color scale. Each of the color regions 115, 120, 125 could be on the bottom surface of the urinal dish 110 so that the user can readily detect which color region 115, 120, 125 corresponds to the urine color as the urine slowly drains out of the urinal dish 110 (draining described below). This urinal dish and corresponding color scale may also be attached to an existing base urinal screen. Any of these components may be integrally formed, provided separately and assembled, or any combination thereof.

The color scale may be water-resistant, regardless of where it is provided on the urine screen 100. This is accomplished, for example, by covering the color regions 115, 120, 125 with a water-resistant layer. The water-resistant layer is transparent so that the color scale remains visible to the user. The water-resistant layer can be a layer of clear plastic such as polyvinyl chloride, polyurethane, low density polyethylene, high density polyethylene, polystyrene, polypropylene and/or polyester, or other suitable materials. The water-resistant layer shown in FIG. 1 is applied on top of each of the color regions 115, 120, 125, but may also be applied to other areas of the base member 105 and/or urinal dish 110.

A water-resistant adhesive may be used to bond the nonabsorbent urine screen 100 to the urinal (or any urine receptacle) so that the nonabsorbent urine screen 100 is held in a fixed position. Using an adhesive allows the urine screen 100 to remain in place while a user applies a urine stream, so that it is easier to deposit urine within the urinal dish 110. Water repeatedly flows over the nonabsorbent urine screen 100 each time the urinal is flushed. A material is thus selected for the water-resistant adhesive that can withstand intermittent flows of water and/or urine. The water-resistant adhesive may be capable of bonding to materials commonly used to construct a urinal or toilet such as porcelain, steel and/or marble. Acrylic adhesives are suitable for these purposes such as the MP690 adhesive sold by Morgan Adhesives Company.

Figure 2:
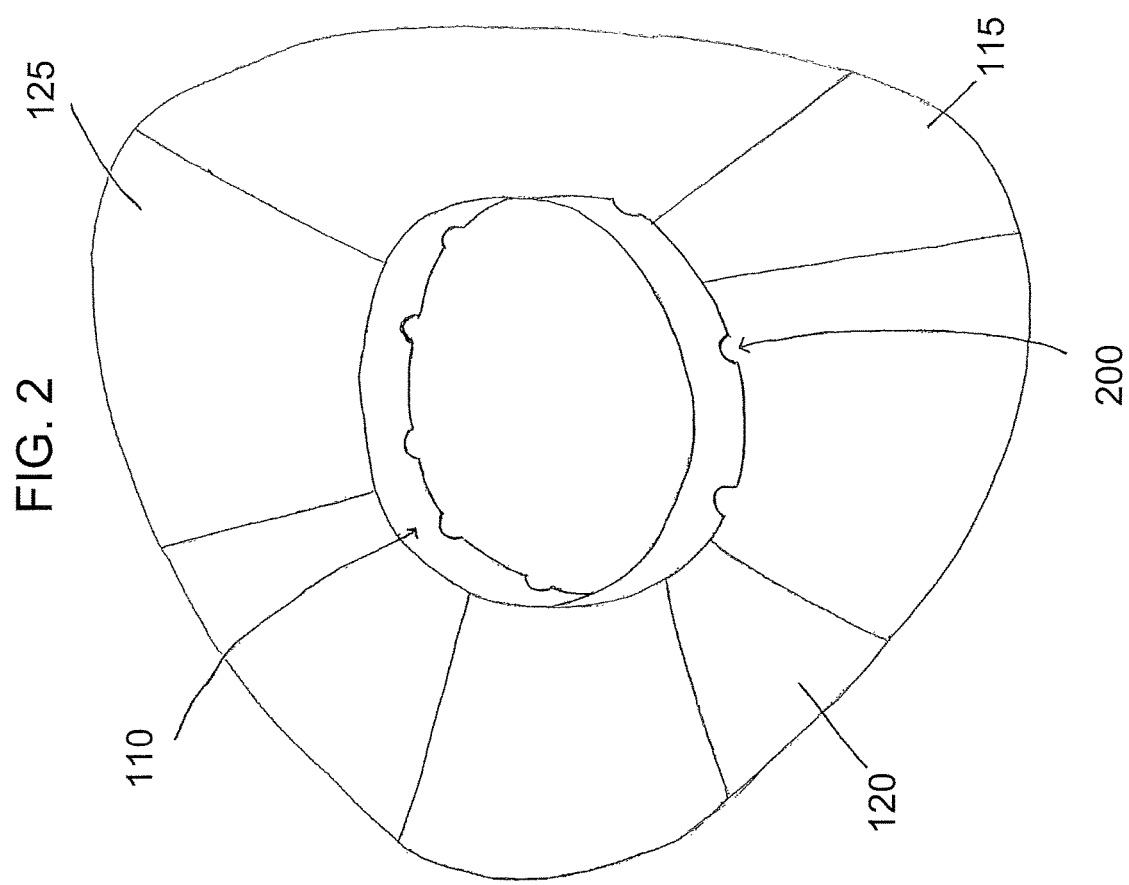
FIG. 2 is a perspective view of the nonabsorbent urine screen.

As illustrated in FIG. 2, the urinal dish 110 includes drain holes 200 so that the urine may be slowly released from the urinal dish 110. The drain holes 200 may be very small in diameter, so that a portion of urine remains in the urinal dish 110 for a period of time (e.g., 3-60 seconds). This controlled, slow draining of urine from the urinal dish 110 allows the user to visually inspect the urine in the urinal dish 110 and compare the urine color to the color scale (e.g., color regions 115, 120, 125). There may be a single drain hole 200 provided in the urinal dish 110 or there may be many drain holes 200. The drain holes 200 may be formed where the side wall of the urinal dish 110 meets the bottom portion of the urinal dish 110 so that the urine fully drains out of the urinal dish 110 over time. The flushing water of the urinal may help to fully drain and cleanse the urine screen 100 (i.e., including the urinal dish 110) so that odors, bacteria, etc. do not develop.

Figure 3:
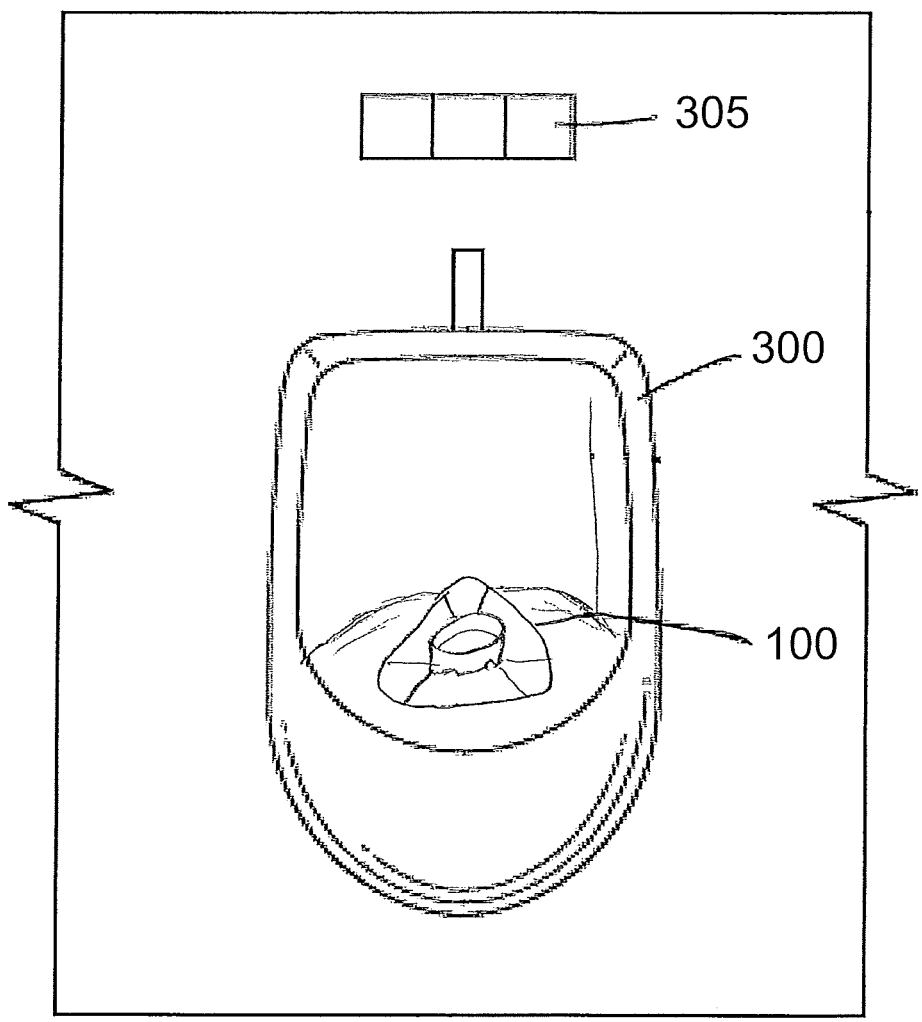
FIG. 3 is a front view of the nonabsorbent urine screen placed in a urinal.

FIG. 3 illustrates an embodiment with the urine screen 100 located within the bowl of a urinal 300. The urine screen 100 may be located near the drain of the urinal 300, and may be upstream of the drain so that the flushing water flows over the urine screen 100.

In one embodiment, as illustrated in FIG. 3, there is a placard 305 that is provided separately from the urinal 300. The placard 305 may be adhered to the wall above the urinal 300 as shown in FIG. 3 or may be provided in any other location (e.g., the user could be holding the placard 305). In one embodiment, the placard 305 may be positioned or fixed at eye-level so that the individual has an unobstructed view of the placard 305 while urinating. The placard 305 may include a second color scale and may include more detailed information than the hydration indicator provided at or near the color regions 115, 120, 125.

Figure 4:
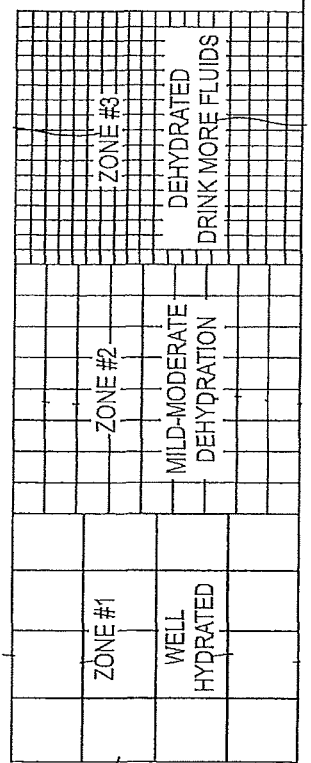
FIG. 4 is a front view of a placard including a second color scale.

FIG. 4 illustrates an example of the placard 305. The second color scale includes a plurality of color regions 415, 420, 425 and hydration level indicators (i.e., the word descriptions on the color regions 415, 420, 425). The layout of the color regions 415, 420, 425 and hydration level indicators may be identical to the color regions 115, 120, 125 and hydration level indicators included on the nonabsorbent urine screen 100, or the hydration level indicators of the color regions 415, 420, 425 on the placard may contain more information. In one embodiment, an identical layout of the color scale of the placard 305 and the color scale of the urine screen 100 is used to help the individual understand how the placard 305 is related to the urine screen 100. This increases the likelihood that the individual will accurately assess his or her hydration level. In one embodiment, the hydration level indicators on the urine screen 100 may simply be a number assigned to each color region, whereas the hydration level indicators on the placard 305 may include both numbers and text describing the hydration level corresponding to each number. As shown in FIG. 4, the placard 305 may also include written instructions describing how to use the nonabsorbent urine screen 100 to determine one's hydration level.

The placard 305 may include an adhesive backing for bonding the placard 305 to the wall. The placard 305 can be made of paper, plastic or any other suitable material. The placard 305 may be water-resistant, but does not have to be water-resistant because it may be positioned so that it is not subject to intermittent flows of water like the nonabsorbent urine screen 100 applied to the urinal.

A method of determining an individual's hydration level will be described with reference to FIGS. 1-3. FIG. 3 illustrates the nonabsorbent urine screen 100 deposited in a urinal 300. The individual applies a stream of urine into the urinal dish 110 of the urine screen 100. As the urine collects in the urinal dish 110, the individual visually compares the urine color to the colors included in the color regions 115, 120, 125 that make up the color scale. The individual may make the comparison after completing urination, or may compare the colors while continuing to urinate.

The user then determines the hydration level by referencing the hydration level indicator associated with the identified color or by using the placard 305 illustrated in FIG. 4 and described above. For example, if the urine color matches a color included in the color region 115, the user determines the hydration level by reading the hydration level indicator stating "Well-Hydrated". As the urinal dish 110 fills with urine, some of the urine slowly drains out through the drain holes 200. However, the urinal dish 110 and drain holes 200 are sized so that a portion of the applied urine will be held within the urinal dish 110 at least for a temporary period so that the user may make the visual comparison between the color scale and the urine color. The individual may flush the urinal by operating a plumbing fixture attached to the top of the urinal after the individual is finished urinating. The plumbing fixture opens a valve that allows water to flow over the urinal screen 100 to flush any residual urine out of the urinal dish and to clean the urine screen 100.

In an alternate embodiment of the method disclosed here, the individual may move the location of the stream of urine as it is being applied so that the urine flows over different color regions 115, 120, 125. In this alternate embodiment, the user visually compares the urine color to the color region 115, 120, 125 as it is being applied to identify a color on the color scale which most closely matches the urine color.

The above-described method does not require the individual to collect or handle the urine any differently than he or she would during a normal voiding process. Sanitary concerns are therefore less likely to discourage individuals from using the nonabsorbent urine screen 100. The urine color can be assessed during the normal voiding process, and so there is no additional time burden placed on the individual to determine his or her hydration level. The relative quickness of the hydration level determination benefits individuals performing physically strenuous tasks under time constraints, such as members of the military, firefighters, manual laborers and athletes.

The nonabsorbent urine screen 100 described above is not limited to being disposed within a urinal. The nonabsorbent urine screen 100 can be applied to urine receptacles besides a urinal or toilet.

Figure 5:
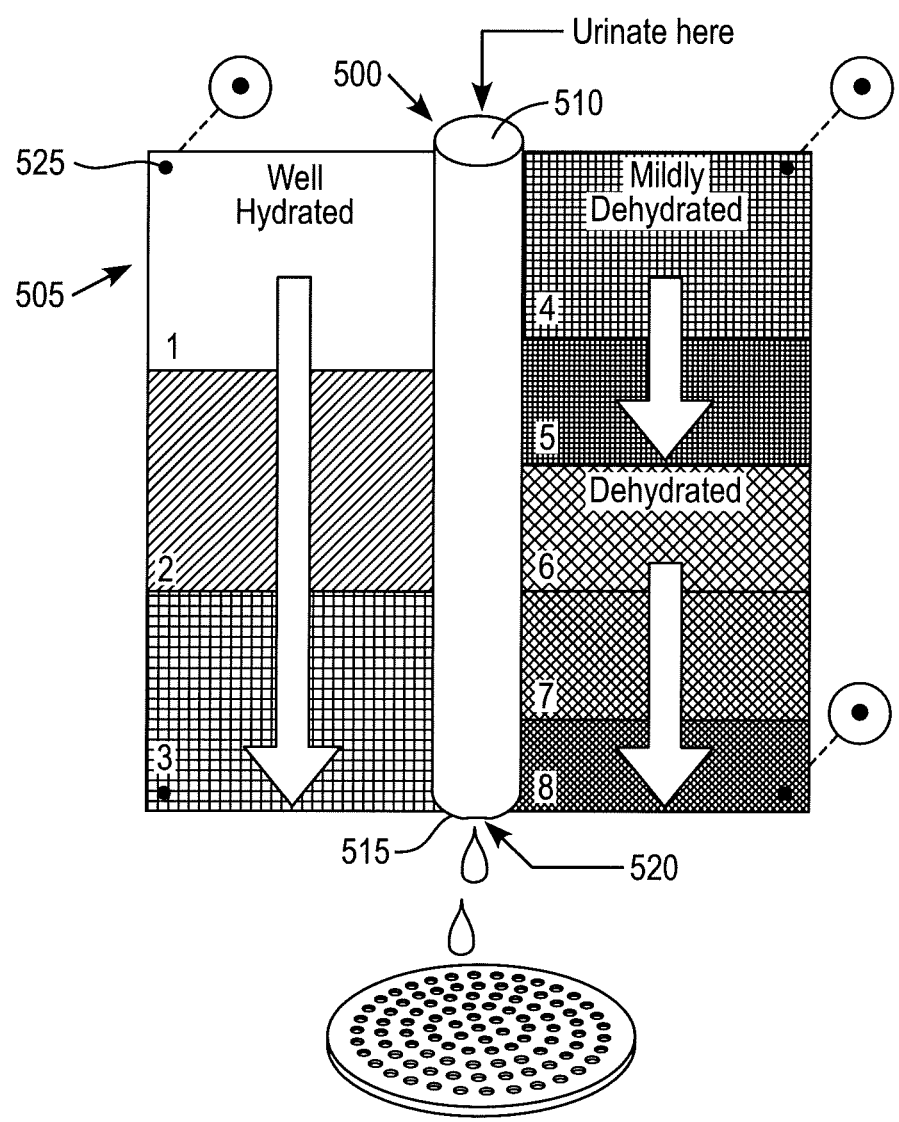
FIG. 5 is a front view of a vertical embodiment of a urinal collective device and a dehydration detection system.

FIG. 5 illustrates an embodiment of a urine collection device and dehydration detection system for determining a hydration level based on urine color. The dehydration detection system includes the vertical urine collection device 500 and the color scale 505. The urine collection device 500 is a largely a hollow cylindrical body that extends in a vertical direction when applied within a urine receptacle. The urine collection device 500 includes an open top portion 510 and a closed bottom portion 515. A user may thus apply a stream of urine through the open top portion 510 so that the urine collection device 500 begins to fill with urine. The bottom portion 515 includes a small drain hole 520 (i.e., a slow drip drainage hole). The small drain hole 520 is sized so that a portion of urine will remain within the cylindrical portion of the urine collection device 500 for enough time for a user to determine the urine color. A plurality of small drain holes 520 may be provided as long as they are appropriately sized. Additionally, the urine collection device 500 may be entirely transparent or may be partially transparent to allow a user to view the color of the urine held within the urine collection device 500.

The urine collection device 500 may be attached to an interior of a toilet bowl, against a vertical side wall of a urinal, or any other similar urine receptacle. The urine collection device 500 could also be a stand-alone device as long as the device is positioned or held to drain into an appropriate location/drain.

The color scale 505 may be attached to a wall or another surface by using fastening members 525. Any fasteners may be utilized for the fastening members 525 to affix the color scale 505 to a structure. For example, the fastening members 525 could be screws, bolts, nails, etc. or a joining method such as welding, soldering, brazing, gluing, etc., or any combination thereof. The color scale 505 may include a series of zones as depicted in FIG. 5 to illustrate dehydration levels. The color scale 505 may also or in addition include any of the features of the color scales discussed above for any of the other embodiments. The color scale 505 may include a plurality of shades of yellow, with each of the shade of yellow corresponding to a hydration level based on urine color. The color scale 505 may also include identifiers (e.g., words and/or numbers) to convey information to the user allowing the user to determine hydration level based on urine color.

Figure 6:
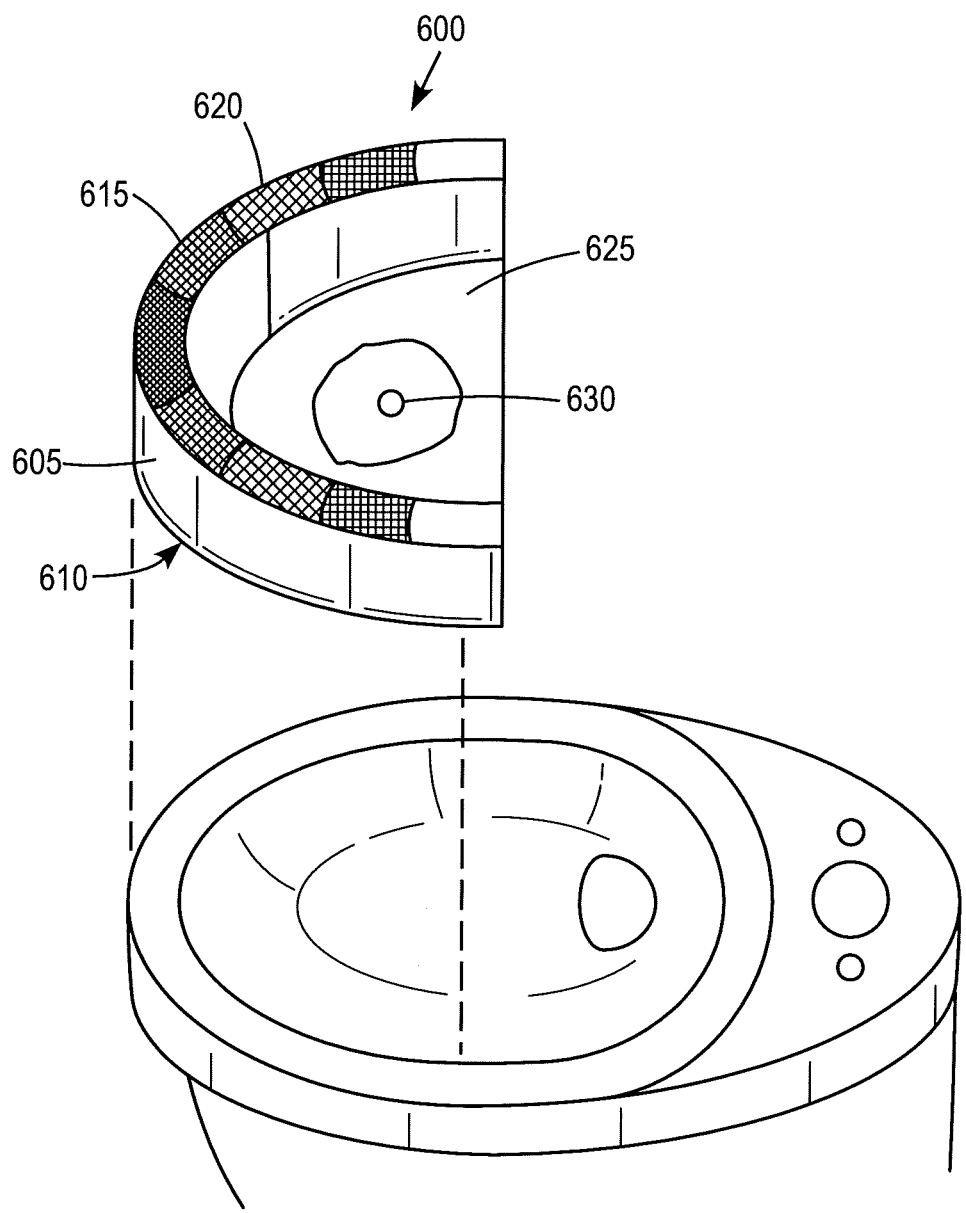
FIG. 6 is a perspective view of a urine collection dish that fits on a toilet.

FIG. 6 illustrates a urine collection dish 600 that fits onto the front portion of a toilet. The urine collection dish 600 includes an attachment portion 605 that attaches at the front rim of the toilet bowl (i.e., the front of the toilet bowl is located opposite of where the drain/flushing mechanism is located). The attachment portion 605 of the urine collection dish 600 may be shaped so that the shape of the urine collection dish 600 matches the contour of the toilet bowl (e.g., arc-shaped or shaped to match the ovular or circular shape of the toilet bowl). The attachment portion 605 extends vertically upward between a lower surface 610 and an upper surface 615. The lower surface 610 of the attachment portion 605 attaches directly to the toilet bowl. The upper surface 615 has a color scale 620 applied on it. A user of the toilet may thus view the color scale 620 on the upper surface 615 of the attachment portion 605 when the user is seated on the toilet. The color scale 620 may include a series of zones as depicted in FIG. 6 to illustrate dehydration levels. The color scale 620 may also or in addition include any of the features of the color scales discussed above for any of the other embodiments, including other visual identifiers of hydration levels. In a modification of this embodiment, the color scale 620 may also be provided separately from the urine collection dish (e.g., as a placard affixed to a wall of the restroom or of the bathroom stall).

The attachment portion 605 may be permanently or removably connected to the toilet bowl. The lower surface 610 of the attachment portion 605 may be adhered to the upper surface of the front portion of the toilet bowl or may be fastened to the toilet bowl in any other manner.

The urine collection dish 600 also includes a dish portion 625 that collects/receives a stream of fluid (e.g., urine). The dish portion 625 may extend outwardly from the lower surface 610 of the attachment portion 605 as illustrated in FIG. 6. The dish portion 625 and the attachment portion 605 may be formed as one integral component (i.e., a unitary structure formed at the same time). The attachment portion 605 and the dish portion 625 could also be two different components that are later assembled/connected together. The dish portion 625 may extend above the bowl of the toilet so as to be above any flushing water within the toilet. In other words, the fluid contained in the dish portion 625 of the urine collection dish 600 may be separated from the flushing water. The dish portion 625 thus may hold urine separately from the flushing water so that the urine color is not diluted/altered by the water. This can allow a user to receive a more accurate urine color reading.

The dish portion 625 may be any shape that allows for a fluid (e.g., urine) to collect within the dish portion 625 to be funneled towards the small drain hole 630. For example, the dish portion 625 may be frustroconically shaped, conically shaped, shaped as an inverted pyramid, parabolically shaped, or any other shape. The small drain hole 630 may be sized similarly as described above so that the fluid (e.g., urine) remains within the dish portion 625 for a sufficient duration of time for a user to determine and compare the urine color to the color scale 620.

FIG. 7 illustrates another embodiment of the urine screen disclosed in this application. The urine screen 700 illustrated in FIG. 7 includes a plurality of color zones 705, 710, 715, 720, 725, 730, 735. Each of the color zones 705, 710, 715, 720, 725, 730, 735 is a progressively darker shade of yellow. These color zones 705, 710, 715, 720, 725, 730, 735 thus depict a range of hydration levels from very hydrated (euhydration in, for example, zones 705 and 710) to moderately hydrated (e.g., mild-moderate dehydration in zones 715 to 725) to severe dehydration (e.g., zones 730 and 735). The urine screen 700 includes a raised edge 740 that defines the outer rim of a urinal dish 745. The urinal dish 745 includes drain holes 750 that allow urine in the urinal dish 745 to drain out of the urinal dish 745 at a predetermined flow rate over a period of time.

The urine screen 700 depicted in FIG. 7 also includes a plurality of mesh holes 755 beneath the urinal dish 745 and beneath the color zones 705, 710, 715, 720, 725, 730, 735. The mesh holes 755 may also extend along the outer periphery upwards to be adjacent to the color zones 705, 710, 715, 720, 725, 730, 735 and the urinal dish 745. The mesh holes 755 allow urine to flow to the drain of the urinal. The areas of the urine screen 700 between the mesh holes 755 may be a non-absorbent material, such as a plastic. FIG. 7 also illustrates that the urine screen 700 may include a decal area 760 where a logo of a sponsor may be displayed. For example, the decal area 760 may be utilized to apply an advertisement and/or a company's logo.

FIGS. 8A and 8B illustrate another embodiment of the urine screen 800. The urine screen 800 includes a raised edge that creates a trough 805 towards the upper edge of the urine screen 800 as shown in FIG. 805. The trough 805 may possess an elliptical shape as illustrated in FIG. 8A, but the trough 805 shape is not limited to being elliptically shaped. For example, the trough 805 may possesses any other shape, such as a rectangular, circular, or hexagonal shape.

In this embodiment, the trough 805 overlaps with a portion of the plurality of the color zones 810, 815, 820, 825, 830, 835. Specifically, the trough 805 is positioned directly above the central color zones 815, 820, 825, 830, and laterally between the two outermost color zones 810 and 835. The user may thus quickly and conveniently compare the color of urine in the trough 805 with the color zones 810, 815, 820, 825, 830, 835. FIG. 8A illustrates seven color zones, but the number of color zones is certainly not limited to seven. Any number of color zones may be selected. The color zones 810, 815, 820, 825, 830, 835 each may be progressively darker, so that depict a range of hydration levels from very hydrated (euhydration in, for example, zone 810) to moderately hydrated (e.g., mild-moderate dehydration in zones 815 to 830) to severe dehydration (e.g., zone 835). The range of hydration levels could also be inversed in some embodiments, so that the greater dehydration zones are instead on the left side of the urine screen 800 (from the viewpoint of the user).

As discussed above, a raised edge of the urine screen 800 may define the trough 805. A side view of the trough 805 is illustrated in FIG. 8B. The raised edges of the trough 805 thus allow urine to collect within the trough 805 so that a user may visibly compare their urine color to the color zones 810, 815, 820, 825, 830, 835. The urine screen 800 may include a sloped top end surface 840. As shown in FIGS. 8A and 8B, this sloped top end surface 840 may direct urine flow towards/into the trough 805. It thus may be easier for a user to apply a stream of urine into the trough 805 because the sloped top end surface 840 may help direct urine into the trough 805. In some embodiments, the sloped top end surface 840 may be another shape. For example, the sloped top end surface 840 could be inwardly curved (i.e., curved towards the urinal at the center with the lateral outer portions of the sloped top end surface 840 protruding away from the urinal) to direct urine towards the center of the trough 805.

Similar to embodiments discussed above, the trough 805 may include drain hole(s) to allow urine to flow out of the trough 805 at a predetermined flow rate based on the diameter of the drain hole(s). In some embodiments, the trough 805 may not include drain hole(s) and instead flushing water of the urinal may be relied on to remove urine from the trough 805.

The urine screen 800 also may include holes 845 (e.g., mesh holes) to allow urine and water to flow therethrough. The holes 845 may be positioned at the periphery of the urine screen 800, so that the holes 845 are on the outer edges of the color zones 810, 815, 820, 825, 830, 835. The number and configuration of these holes 845 is not particularly limited.

Figure 9:
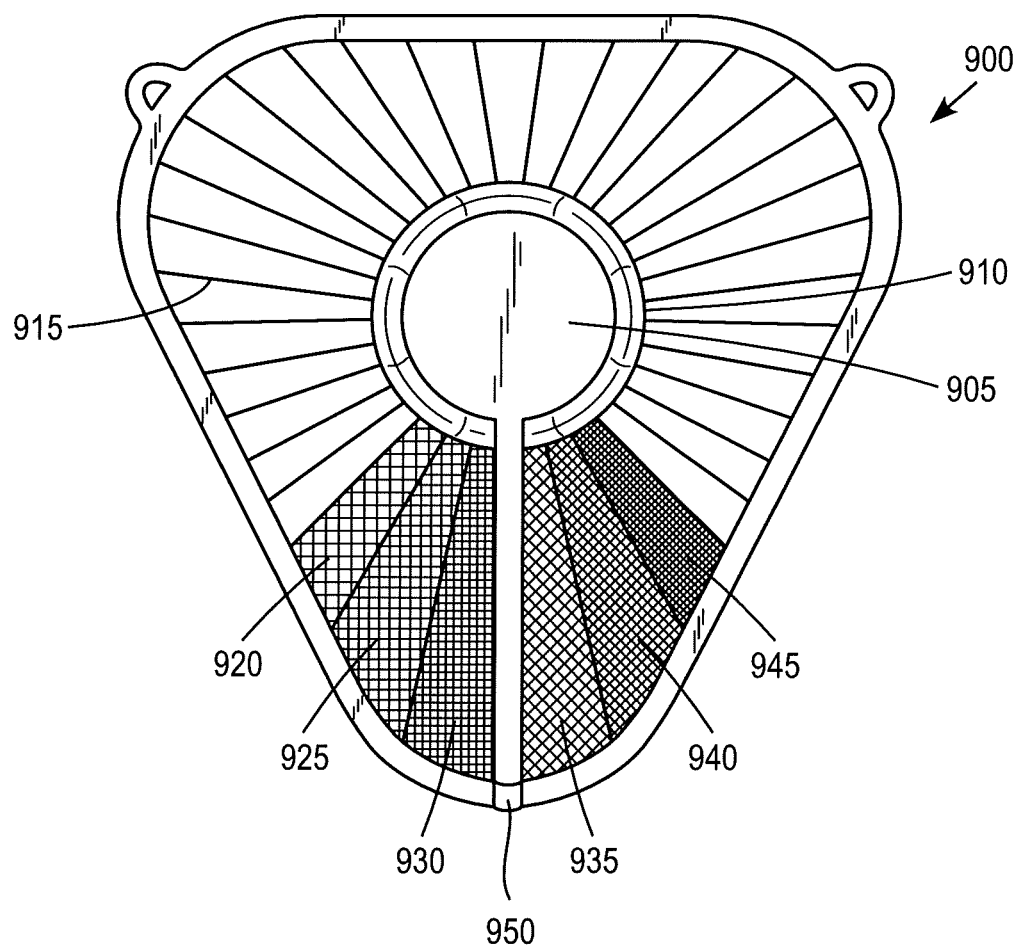
FIG. 9 is a top view of an embodiment of a urine screen.

FIG. 9 illustrates an embodiment of a urine screen 900 that includes a central urinal dish 905. The urinal dish 905 is configured to at least temporarily hold a liquid (e.g., urine). The urinal dish 905 thus may include a raised edge (e.g., similar to the trough in the FIG. 8A embodiment described above) or may be a recessed portion that extends vertically below the urine screen 900. The urinal dish 905 may include a plurality of small drain holes 910. The size of the diameter of the small drain holes 910 may be selected to ensure a specific flow rate of urine out of the urinal dish 905. For example, the small drain holes 910 may be sized to allow an average supply of urine to flow completely out of the urinal dish 905 in a range of 7 to 15 seconds. The small drain holes 910 may alternatively be sized to cause urine to be held in the urinal dish 905 for any other time period desired.

The urine screen 900 shown in FIG. 9 includes a plurality of extension portions 915 extending from the urinal dish 905 to the outer periphery of the screen 900. These extension portions 915 that form the urine screen 900 may be a flexible plastic that does not absorb water. For example, the extension portions 915 may be a clear plastic such as polyvinyl chloride, polyurethane, low density polyethylene, high density polyethylene, polystyrene, polypropylene and/or polyester, or other suitable materials.

The urine screen 900 includes six color zones 920, 925, 930, 935, 940, 945. These six color zones 920, 925, 930, 935, 940, 945 may be colored to progressively indicate greater levels of dehydration, as discussed above. Six color zones are shown for exemplary purposes, but the number of color zones is not limited to six. One aspect of the embodiment in FIG. 9 is that the color zones 920, 925, 930, 935, 940, 945 are formed directly on the extension portions 915 to extend between adjacent extension portions 915. This design allows for a simple, compact urine screen 900 to be manufactured.

FIG. 9 also illustrates that a drain channel 950 be extend downwards from the urinal dish 905. The drain channel 950 is a fluid passageway that allows liquid (e.g., urine) to flow out of the urinal dish 905. In embodiments where the drain channel 950 is provided, the small drain holes 910 may be omitted. The size of the drain channel 950 may be selected to ensure a specific flow rate of urine out of the urinal dish 905 as described above. The drain channel 950 may be uncovered (or include a transparent top portion) so that a user may visibly detect the color of urine flowing through the drain channel 950 to compare the urine color with the color zones 920, 925, 930, 935, 940, 945. The drain channel 950 may thus both facilitate the user's visible dehydration level comparison, while also transporting urine out of the urinal dish 905 for sanitary purposes.

Figure 10A:
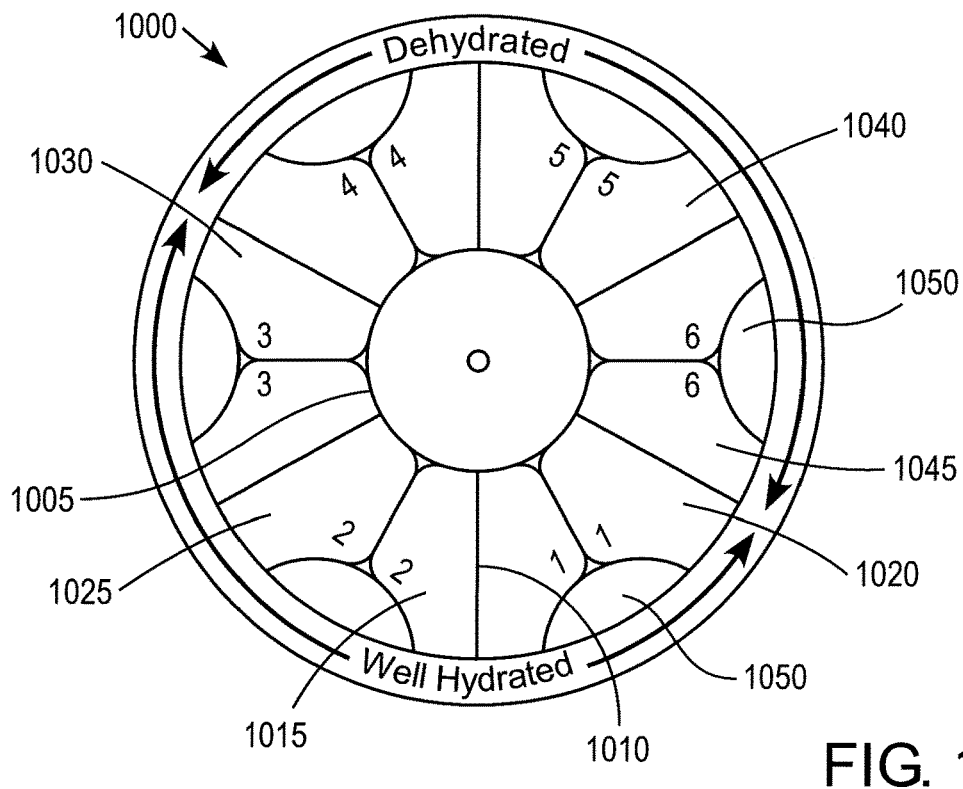
FIGS. 10A and 10B are views of an embodiment of a urine screen.
Figure 10B:
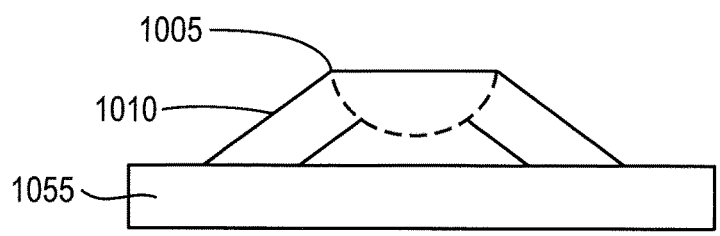

FIGS. 10A and 10B illustrate an embodiment of a urine screen 1000 that includes a raised central urinal dish 1005. FIG. 10A shows the top view of the urine screen 1000 and FIG. 10B shows a side view. The side view of FIG. 10B illustrates that the urine screen 1000 possesses a profile with a downwardly sloping shape, i.e., there are downwardly sloping surfaces 1010 extending away from the raised edges (that define the urinal dish 1005). The urinal dish 1005 thus may be in a central raised portion of the urine screen 1000. The downwardly sloping surfaces 1010 may be spaced apart from one another (e.g., evenly spaced apart) to define different dehydration level zones. The faces 1015 between the downwardly sloping surfaces 1010 may be colored to indicate dehydration levels as described in the various embodiments above. The faces 1015 may instead or in addition include numbering and/or lettering to reflect dehydration levels. FIG. 10A illustrates six color zones 1020, 1025, 1030, 1035, 1040, 1045, but the number and orientation of the color zones is not limited in any manner.

The urinal screen 1000 may include one or more color comparator dishes 1050. For example, FIG. 10A shows that there is one color comparator dish 1050 in each of the six color zones 1020, 1025, 1030, 1035, 1040, 1045. The color comparator dish 1050 may collect urine in the immediate vicinity of one of the six color zones 1020, 1025, 1030, 1035, 1040, 1045. A user may thus apply urine into a specific color comparator dish 1050 to compare the urine color to a specific zone. For example, a user may: (i) apply some urine into the central urinal dish 1005, (ii) make an assessment about which color zone 1020, 1025, 1030, 1035, 1040, 1045 appears to be the closest to the urine color, and (iii) then apply additional urine into the color zone 1020, 1025, 1030, 1035, 1040, 1045 that appeared to be closest. The color comparator dish(es) 1050 thus may allow a user to confirm their dehydration level more accurately.

The central urinal dish 1005 and the one or more color comparator dishes 1050 may include one or more small drain holes as discussed above in other embodiments. In other embodiments, the central urinal dish 1005 and the one or more color comparator dishes 1050 may not include drain holes and may instead be flushed/cleaned by the urinal flushing water flowing into/through the central urinal dish 1005 and the one or more color comparator dishes 1050 during a flushing operation.

The urine screen 1000 may include a circular base member 1055. The sloping surfaces 1010 extend upwards from the circular base member 1055. The base member 1055 can also be another shape or configuration instead of being circular. The base member 1055 may be applied directly to the interior of a urinal, and may be flexible so that the base member 1055 deforms to match the contour of the urinal.

Figure 11:
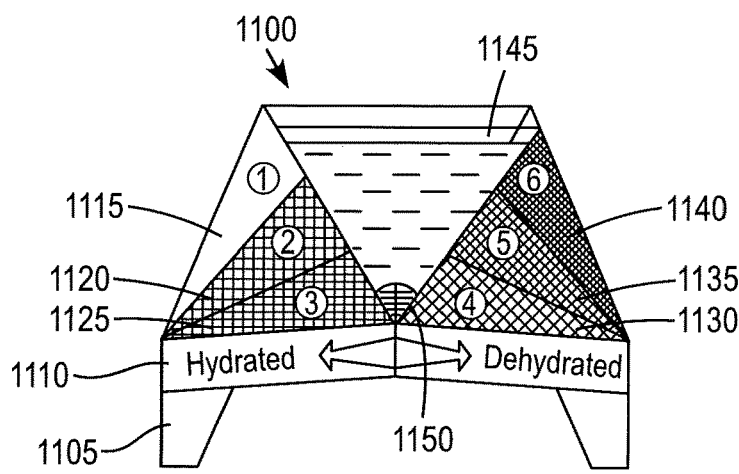
FIG. 11 is a front view of an embodiment of a urine receptacle.

Another embodiment of a urine screen is shown in FIG. 11 as a raised urine receptacle 1100. The urine receptacle 1100 may be placed directly into a urinal, but also may be positioned in another location (e.g., toilet) to receive urine. The urine receptacle 1100 may extend upwardly from elevation legs 1105. Two legs 1105 are shown in FIG. 11, but the number of legs is not limited thereto. The urine receptacle 1100 includes a base member 1110 that extends between the elevation legs 1105. The base member 1110 may include hydration level indications. For example, FIG. 11 shows that one section of the base member 1110 is labeled "HYDRATED" and another section of the base member 1110 is labeled "DEHYDRATED".

The urine receptacle 1100 may then include color zones 1115, 1120, 1125, 1130, 1135, 1140 positioned above the base member 1110. These color zones 1115, 1120, 1125, 1130, 1135, 1140 may reflect a hydration level as described above. The number of color zones is not limited in any respect. Three of the color zones 1115, 1120, 1125 may reflect that the user is hydrated and may thus be positioned above the section of the base member 1110 labeled "HYDRATED". Similarly, three of the color zones 1130, 1135, 1140 may reflect that the user is dehydrated and may thus be positioned above the section of the base member 1110 labeled "DEHYDRATED".

The central portion of the urine receptacle 1100 above the base member 1110 may be a urinal dish 1145. The urinal dish 1145 may be shaped to collect a fluid (e.g., urine). For example, the urinal dish 1145 can be frustroconically shaped, conically shaped, shaped as an inverted pyramid, parabolically shaped, or possess any other shape. The base member 1100 may include one or more drain holes 1150 that allows fluid in the urinal dish 1145 to drain out of the urinal dish 1145 (i.e., due to gravity). The size and configuration of the drain holes 1150 may be specifically selected in the same manner as discussed above in other embodiments (e.g., to allow urine collection for a predetermined amount of time based on a drainage flow rate).

Figure 12A:
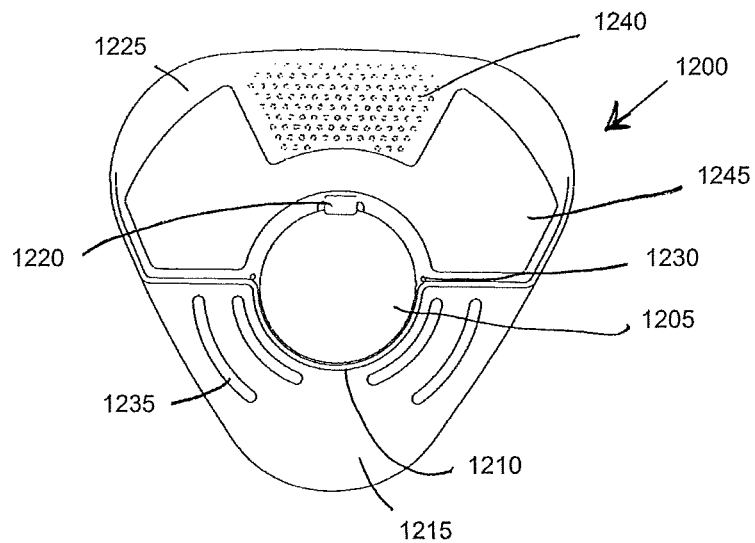
FIGS. 12A and 12B illustrate an embodiment of a urine screen.
Figure 12B:
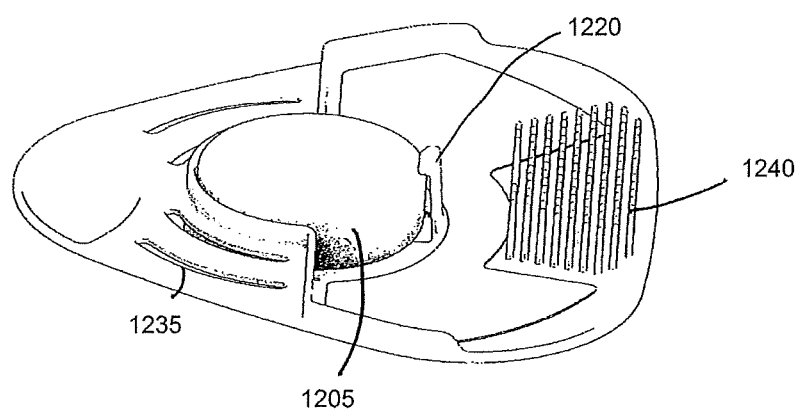

FIGS. 12A and 12B illustrate another embodiment of a urine screen 1200. The urine screen 1200 includes a urinal puck 1205 (i.e., a urinal deodorizer block or urinal cake) as part of the design. The urinal puck 1205 is positioned between a raised edge 1210 of the bottom part 1215 of the urine screen 1200 and a clasping member 1220 of the upper part of the urine screen 1200. The clasping member 1220 may be bent/pulled away from the raised edge 1210 to insert a new urinal puck 1205. The clasping member 1220 may then elastically return to a clasping position to secure the urinal puck 1205 in place.

The urine screen 1200 may include small drain holes 1230 on either lateral side of the urinal puck 1205 as shown in FIG. 12A. The number and position of the small drain holes 1230 is not limited thereto. The bottom part 1215 of the urine screen 1200 may also include one or more drain slots 1235. FIGS. 12A and 12B illustrate four drain slots 1235 (i.e., two on each lateral side of the urine screen 1200), but the number of drain slots 1235 is not limited. The small drain holes 1230 and the drain slots 1235 allow for fluids (e.g., urine and water) to flow through the urine screen 1200 to a drain of the urinal.

The upper part 1225 of the urine screen 1200 may include a plurality of raised fingers 1240. The raised fingers 1240 may be resilient, flexible protrusions, for example, formed out of a plastic material. The raised fingers 1240 may be utilized to disperse applied urine to minimize splashing of the urine. In other words, urine applied onto the raised fingers 1240 may be dispersed and redirected to smoothly flow towards the urinal puck 1205, the small drain holes 1230, and the drain slots 1235.

A color scale may be provided along the upper part of the urine screen 1200. For example, a plurality of color zones and/or other hydration level indications may be applied/printed onto this area of the urine screen 1200 in a similar manner as described above for other embodiments. Urine may collect in the recessed portion 1245 to allow a user to visually identify their hydration level. The recessed portion 1245 may include portions of (or the entirety of) the color scale in some embodiments.

It is further noted that the urinal puck 1205 itself could be hollow (cylindrically shaped) to serve as a urine dish. A user could thus deposit urine into the hollow urinal puck 1205 to compare the urine color to the color zones. Over time, the urinal puck 1205 would erode, and so a replacement urinal puck 1205 would periodically be required.

While the invention has been described in connection with various embodiments, it will be understood that the invention is capable of further modifications. The various aspects of the different illustrative embodiments may be added/combined into other embodiments. This application is intended to cover any variations, uses or adaptations of the invention following, in general, the principles of the invention, and including such departures from the present disclosure as, within the known and customary practice within the art to which the invention pertains.

What is claimed is:

1. A nonabsorbent urine screen for determining a hydration level based on urine color while being placed in a urinal, the nonabsorbent urine screen comprising:

a base member possessing a front side and a back side, the base member being dimensioned to be positioned in the urinal;

a urinal dish comprising a side wall that extends from the front side of the base member and an open top portion, the urinal dish configured to receive fluid into the urinal dish through the open top portion, and the urinal dish comprising a drain hole; and a color scale fixed to the front side of the base member, the color scale including at least a plurality of shades of yellow, each of the shades of yellow corresponding to a hydration level based on urine color, wherein the urine screen is nonabsorbent, the base member is a plastic screen, the urinal dish is plastic, the base member comprises an interior portion and a peripheral portion entirely surrounding the interior portion, the side wall of the urinal dish extending around the interior portion of the base member so that the urinal dish is positioned at the interior portion of the base member entirely within the peripheral portion of the base member, and the color scale being fixed to the peripheral portion of the base member beyond the urinal dish at the interior portion of the base member.

2. The nonabsorbent urine screen of claim 1, wherein the urinal dish comprises a plurality of drain holes.

3. The nonabsorbent urine screen of claim 1, wherein the color scale is adhered to the front side of the base member at the peripheral portion of the base member using a water-resistant adhesive.

4. The nonabsorbent urine screen of claim 1, wherein the urinal dish is a trough created by a protruding edge extending upwards from the base member.

5. The nonabsorbent urine screen of claim 1, further comprising a transparent, water-resistant layer covering at least the color scale.

6. The nonabsorbent urine screen of claim 1, wherein the color scale is applied at three spaced apart locations on the base member.

7. The nonabsorbent urine screen of claim 1, wherein the base member is triangularly shaped.

8. The nonabsorbent urine screen of claim 7, wherein the triangularly-shaped base member comprises three rounded corners.

9. The nonabsorbent urine screen of claim 8, wherein the side wall of the urinal dish is circular such that a cross-section of the urinal dish is circular.

10. The nonabsorbent urine screen of claim 1, wherein the side wall of the urinal dish extends 4 mm-5 mm from the base member.

11. The nonabsorbent urine screen of claim 7, wherein the base member is planar when no external force is applied thereon.

12. The nonabsorbent urine screen of claim 6, wherein
the base member is triangularly shaped and comprised of three corners, and
the three spaced apart locations on the base member are at each of the three corners of the base member.

13. The nonabsorbent urine screen of claim 1, further comprising a water-resistant layer adhered to the base member and the urinal dish, the water-resistant layer being a clear plastic.

* * * * *